United States Patent
Liu et al.

(10) Patent No.: US 12,048,726 B2
(45) Date of Patent: Jul. 30, 2024

(54) **METHOD FOR EXTRACTING *GYMNADENIA CONOPSEA* AND RELATED *GYMNADENIA CONOPSEA* EXTRACT**

(71) Applicant: SHANGHAI HOPE-TEC BIOTECHNOLOGY INC., Shanghai (CN)

(72) Inventors: Xing Liu, Shanghai (CN); Jibin Wang, Shanghai (CN); Haihua Chen, Shanghai (CN); Zuokun Ding, Shanghai (CN); Chuanhao Wang, Shanghai (CN); Jiwen Wang, Shanghai (CN)

(73) Assignee: Shanghai Hope-Tec Biotechnology Inc., Shanghai (CN)

( * ) Notice: Subject to any disclaimer, the term of this patent is extended or adjusted under 35 U.S.C. 154(b) by 513 days.

(21) Appl. No.: 17/441,573

(22) PCT Filed: Apr. 1, 2020

(86) PCT No.: PCT/CN2020/082792
§ 371 (c)(1),
(2) Date: Sep. 21, 2021

(87) PCT Pub. No.: WO2020/207313
PCT Pub. Date: Oct. 15, 2020

(65) Prior Publication Data
US 2022/0160811 A1 May 26, 2022

(30) Foreign Application Priority Data
Apr. 8, 2019 (CN) .......................... 201910274935.1

(51) Int. Cl.
*A61K 36/898* (2006.01)
*A61K 8/9794* (2017.01)
(Continued)

(52) U.S. Cl.
CPC .......... *A61K 36/898* (2013.01); *A61K 8/9794* (2017.08); *A61Q 19/02* (2013.01); *A61Q 19/08* (2013.01); *A61K 2236/13* (2013.01); *A61K 2236/15* (2013.01); *A61K 2236/331* (2013.01); *A61K 2236/37* (2013.01); *A61K 2236/53* (2013.01)

(58) Field of Classification Search
None
See application file for complete search history.

(56) References Cited

FOREIGN PATENT DOCUMENTS

| CN | 101647958 A | 2/2010 |
| CN | 103535731 A | 1/2014 |

(Continued)

OTHER PUBLICATIONS

Yang, M., Study on Polysaccharides Characteristics from Gymnadenia Conopsea R.Br., China Master's Theses Full-text Database_Medicine and Health Technology, No. 03, Mar. 15, 2013. (Year: 2013).*

(Continued)

*Primary Examiner* — Dominic Lazaro
(74) *Attorney, Agent, or Firm* — MOSER TABOADA

(57) ABSTRACT

The present disclosure provides a method for extracting *Gymnadenia conopsea*(L.)R.Br., which includes the following steps: (1) the root tuber of *Gymnadenia conopsea*(L.) R.Br. is soaked in water so that it can be fully infiltrated until having been taken as a sample, no white core is observed; (2) the root tuber of *Gymnadenia conopsea*(L.)R.Br. is ultra-finely comminuted by wet method to obtain a dispersion slurry; (3) additional water is supplemented into the dispersion slurry to obtain diluted dispersion followed by heating and adding neutral protease, and then extraction is carried out through circulation and homogenization by the homogenization pump to obtain extracted material fluid; (4) heat preservation and enzyme inactivation; (5) coarse filtration to obtain a coarse filtrate; and (6) fine filtration to obtain a fine filtrate. The disclosure also provides a related extract of *Gymnadenia conopsea*(L)R.Br.

18 Claims, 2 Drawing Sheets

(51) Int. Cl.
   *A61Q 19/02*    (2006.01)
   *A61Q 19/08*    (2006.01)

(56) References Cited

FOREIGN PATENT DOCUMENTS

| CN | 108619017 A | 10/2018 |
|---|---|---|
| CN | 109939057 A | 6/2019 |
| KR | 10-2003-0061756 A | 7/2003 |
| WO | WO2009139231 A1 | 11/2009 |

OTHER PUBLICATIONS

Zhang, Xiaohong et al., "The Structural Analysis of Gymnadenia Conopsea Polysaccharide", Journal of Inner Mongolia University (Natural Science Edition), vol. 36, No. 02, Mar. 31, 2005 (Mar. 31, 2005), pp. 148-151.

Sun, Ping et al., "Study on the Extraction of Polyasccharides from Gymnadenia conopsea R.Br.", Food Research and Development, vol. 31, No. (03), Mar. 31, 2010 (Mar. 31, 2010), pp. 76-79.

Yang, Mingming., "Study on Polysaccharides Characteristics from Gymnadenia Conopsea R.Br.", China Master's Theses Full-Text Database_Medicine and Health Technology, No. 03, Mar. 15, 2013 (Mar. 15, 2013), pp. 9, 10, 27, 31, 32.

Lin, Peng-Cheng et al., "Characterization and comparison of bioactive polysaccharides from the tubers of Gymnadenia conopsea", Food Hydrocolloids, vol. 43, May 28, 2014 (May 28, 2014), pp. 199-206.

International Search Report for Application No. PCT/CN2020/082792 dated Jun. 30, 2020.

\* cited by examiner

METHOD FOR EXTRACTING *GYMNADENIA CONOPSEA* AND RELATED *GYMNADENIA CONOPSEA* EXTRACT

CROSS-REFERENCE TO RELATED APPLICATIONS

The present application is a U.S. National Stage entry under 35 U.S.C. § 371 based on International Application No. PCT/CN2020/082792, filed on Apr. 1, 2020, which claims the priority of Chinese Patent Application 201910274935.1, filed Apr. 8, 2019, the complete contents of which patent documents are incorporated herein by reference.

TECHNICAL FIELD

The present disclosure relates to the field of plant extraction, in particular to the field of the extraction from *Gymnadenia conopsea*(L.)R.Br, specifically, an extraction method and related extract of *Gymnadenia conopsea*(L.)R.Br.

BACKGROUND

*Gymnadenia conopsea*(L.)R.Br, also known as *Gymnadenia* R.Br, *Gymnadenia conopsea* R., Conic *Gymnadenia* Rhizome, is the root tuber of Orchidaceae plant *Gymnadenia conopsea* or *Gymnadenia* crassinervis Finet.

*Gymnadenia conopsea*(L.)R.Br is distributed in Northeast China, North China, Northwest China, Sichuan, Yunnan, Qinghai and Tibet, especially those grown in Tibet has the best quality. *Gymnadenia conopsea*(L.)R.Br from Tibet, which is called Wangla by Tibetans and Tibetan doctors, has a very high medicinal value. People in Qinghai-Tibetan Plateau have always regarded ZangWangla as a kind of life-everlasting grass given by God.

*Gymnadenia conopsea*(L.)R.Br has been recorded in many classical Chinese medical classics. In Jingzhu Materia Medica (edited by King of Medicine DiMar danzeng-pengcuo (1673-1743)), which is known as the Tibetan Compendium of Materia Medica, there is recorded that "*Gymnadenia conopsea*(L.)R.Br has the effects of nourishing Essence and tonifying Yang, increasing physical strength, reinforcing vital energy, tranquillizing and improving intelligence, prolonging life and longevity, the plant can only be obtained in a small amount and is rare, has a mild property and long-lasting efficacy".

*Gymnadenia conopsea*(L.)R.Br is rich in a variety of physiological active substances. According to the literature report, *Gymnadenia conopsea*(L.)R.Br contains about 30% by weight of polysaccharide, about 27% by weight of starch, about 20% by weight of protein, about 5% by weight of reducing sugar, calcium oxalate, glycosides, trace elements and minerals etc., which have high edible and medicinal values. For treatment of disease, *Gymnadenia conopsea*(L.)R.Br has the following effects: suppressing cough and calming panting; benefiting kidney and tonifying spleen, rectifying Qi and harmonizing blood, relieving pain, tonifying Qi and replenishing blood, engendering fluid and allaying thirst; treating cough and asthma due to lung deficiency, vacuity consumption and marasmus, neurasthenia, chronic diarrhea, hemorrhage, morbid leucorrhea, hypogalactia, chronic hepatitis, poisoning and diarrhea, and can be used as an agent of nourishing essence and tonifying Yang when being soaked in wine. In food therapy and health care, *Gymnadenia conopsea*(L.)R.Br has the function of nourishing essence and tonifying Yang, which can be used for treating seminal emission, spermatorrhoea, impotence, emaciation and weakness, weak health due to enduring illness, and wandering in mind. *Gymnadenia conopsea*(L.)R.Br can be directly boiled in soup, stewed with chicken, soaked in wine, or taken with milk.

Currently, the forms of products from raw material *Gymnadenia conopsea*(L.)R.Br are mainly crude drug obtained after the root tuber of *Gymnadenia conopsea*(L.)R.Br having been boiled and dried by boiling water, or processed into Chinese Herbal slices, directly oral Chinese Herbal powder. Alternatively, the products from *Gymnadenia conopsea*(L.)R.Br can also be processed into the complex polyphamaceutic Chinese Herbal decoction pieces, Chinese patent drug of pills, pulvis, and capsules, etc., or, it can be prepared into some powder extracted from plant, with a standard proportion. However, there are few reports on the preparation and application of *Gymnadenia conopsea*(L.)R.Br polysaccharide which is the most effective ingredient in *Gymnadenia conopsea*(L.)R.Br, extract of *Gymnadenia conopsea*(L.)R.Br polysaccharide, and extract of *Gymnadenia conopsea*(L.)R.Br. polysaccharide complex.

Chinese patent application (CN106692687A) related to an extraction process of Mongolian medicine *Gymnadenia conopsea* tuber, which was characterized in that *Gymnadenia conopsea* tuber was mixed with milk to make milk-*Gymnadenia conopsea* or milk-*Gymnadenia conopsea* powder, which corresponds to using milk to boil and extract *Gymnadenia conopsea* instead of using boiling (Tang Zhu) water for boiling, and then drying to obtain the dried product of milk-*Gymnadenia conopsea*.

Chinese patent application (CN103120759A) related to an extracting method of conic gymnadenia tuber element, which was characterized in that the plant essence was extracted from *Gymnadenia conopsea* by using $CO_2$ supercritical method.

Chinese patent application (CN103535731A) related to an extracting method of essence material of conic gymnadenia rhizome, which specifically includes the following four steps: extraction with pure water, filtration through microporous membrane, concentration by reverse osmosis membrane and drying of concentrated fluid.

The processes of the above patent applications all involved different solvents or carriers (milk, $CO_2$ and water), but none of them had targeted extraction and/or purification of polysaccharide which is the most effective ingredient in *Gymnadenia conopsea*(L.)R.Br, and of polysaccharide complex of *Gymnadenia conopsea*(L.)R.Br., nor can they determine the content limit and quality characteristics of the *Gymnadenia conopsea*(L.)R.Br. polysaccharide, *Gymnadenia conopsea*(L.)R.Br. polysaccharide complex. Moreover, none of them involved in the application research of *Gymnadenia conopsea*(L.)R.Br polysaccharide and *Gymnadenia conopsea*(L.)R.Br polysaccharide complex in cosmetics.

SUMMARY

In order to overcome the disadvantages in the prior art, one object of the disclosure is to provide a method for extracting *Gymnadenia conopsea*(L.)R.Br, which is unique and novel in process, and the extracted *Gymnadenia conopsea*(L.)R.Br extract has unique application value in the aspects of skin care, wound repair, anti-wrinkle, sunscreen, anti-oxidation, anti-allergy, skin moisturizing, etc., which has good application prospect in the field of cosmetics and is suitable for large-scale application.

Another object of the disclosure is to provide a method for extracting *Gymnadenia conopsea*(L.)R.Br, which has the advantages of ingenious design, simple and convenient operation and low cost, and thus is suitable for large-scale application.

Another object of the disclosure is to provide an extract of *Gymnadenia conopsea*(L.)R.Br, which has unique application value in the aspects of skin care, wound repair, anti-wrinkle, sunscreen, anti-oxidation, anti-allergy, skin moisturizing, etc., has good application prospect in the field of cosmetics and is suitable for large-scale application.

Another object of the disclosure is to provide an extract of *Gymnadenia conopsea*(L.)R.Br, which is obtained by an extracting method with ingenious design, simple and convenient operation and low cost, and thus is suitable for large-scale application.

To achieve the above purpose, the disclosure in the first aspect provides a method for extracting *Gymnadenia conopsea*(L.)R.Br, wherein the method comprises the following steps:
(1) the root tuber of *Gymnadenia conopsea*(L.)R.Br is soaked in water so that it can be fully infiltrated until having been taken as a sample, no white core is observed in the root tuber of *Gymnadenia conopsea* (L.)R.Br.;
(2) the root tuber of *Gymnadenia conopsea*(L.)R.Br is ultrafinely comminuted by wet method to obtain a dispersion slurry;
(3) additional water is supplemented into the dispersion slurry to obtain diluted dispersion slurry followed by heating of the diluted dispersion slurry and adding neutral protease to the diluted dispersion slurry, and then extraction is carried out through circulation and homogenization by the homogenization pump to obtain extracted material fluid;
(4) the extracted material fluid is treated through heat preservation and enzyme inactivation;
(5) the extracted material fluid is subjected to coarse filtration to obtain a coarse filtrate; and
(6) the coarse filtrate is subjected to fine filtration to obtain a fine filtrate.

In some embodiments, in the step (1), the volume (by liter) of water is 40-60 times of the weight (by kilogram) of the root tuber of *Gymnadenia conopsea*(L.)R.Br; or, the temperature of the water is kept between 40° C. and 60° C.

In some embodiments, in the step (2), the ultrafine comminution by wet method is carried out by an ultra-fine crusher used for wet method of traditional Chinese medicine; or, the particle size of the dispersion slurry is 60 to 100 mesh.

In some embodiments, in the step (3), the volume (by liter) of water contained in the diluted dispersion slurry is 40-60 times of the weight (by kilogram) of the root tuber of *Gymnadenia conopsea*(L.)R.Br; or, the diluted dispersion slurry is heated to 40° C. to 60° C.; or, the neutral protease is added in an amount of 0.01% to 1.0% (by weight) relative to the weight of the root tuber of *Gymnadenia conopsea*(L.) R.Br; or, the extracted material fluid has the particle size of 100 to 500 mesh; or the duration of extraction is 1 to 6 hours.

In some embodiments, in the step (4), the temperature of the heat preservation and enzyme inactivation is 75° C. to 90° C., and the duration of the heat preservation and enzyme inactivation is 15 to 30 minutes; or, in step (5), the coarse filtration is a pressure filtration by using a filter cloth with 400 to 1000 mesh and a medium speed filter paper; or, in step (6), the fine filtration is carried out through a filter core with 0.2 to 0.45 μm.

In some embodiments, after the step (6), the extracted method further includes the following steps:
(71) the fine filtrate is concentrated to obtain a concentrated fluid;
(72) ethanol is added to the concentrated fluid for precipitation to obtain precipitate and supernatant;
(73) the precipitate is washed with the ethanol to obtain eluent, and then the precipitate is dried to obtain the *Gymnadenia conopsea*(L.)R.Br polysaccharide; and
(74) the supernatant is combined with the eluent followed by recovery under reduced pressure with dealcoholization, and butanediol is added thereto, thus the extract fluid of *Gymnadenia conopsea*(L.)R.Br. is obtained.

More preferably, in the step (71), the volume (by liter) of the concentrated fluid is 10-40 times of the weight (by kilogram) of the root tuber of *Gymnadenia conopsea*(L.) R.Br; or, in the step (72), the ethanol has a concentration of 70% (v/v) or more; or, in the step (73), the drying is freeze drying, vacuum drying or hot air circulation drying; or, in the step (74), the butanediol is added in an amount of 5% to 50% by weight.

In some embodiments, after the step (6), the method for extracting *Gymnadenia conopsea*(L.)R.Br further includes the following steps:
(81) the fine filtrate is concentrated to obtain a concentrated fluid;
(82) the concentrated fluid is subjected to heat preservation and sterilization followed by a second fine filtration to obtain a second fine filtrate; and
(83) organic acids and/or diols are added into the second fine filtrate to obtain an extract fluid of *Gymnadenia conopsea*(L.)R.Br polysaccharide complex free of preservative.

More preferably, in the step (81), the volume (by liter) of the concentrated fluid is 10-40 times of the weight (by kilogram) of the root tuber of *Gymnadenia conopsea*(L.) R.Br; or, in the step (82), the temperature of heat preservation and sterilization is 80° C. to 100° C., and the duration of heat preservation and sterilization is 15 to 30 minutes; or, the second fine filtration is carried out through a filter core with 0.2 to 0.45 μm; or, in the step (83), the organic acid is p-anisic acid with an adding amount of 0.05% to 0.4% by weight, and the diol is propylene glycol with an adding amount of 5% to 30% by weight.

The disclosure in the second aspect provides an extract of *Gymnadenia conopsea*(L.)R.Br, wherein the extract is prepared by the method for extracting *Gymnadenia conopsea* (L.)R.Br as described above.

The disclosure mainly has the following beneficial effects:
1. The method for extracting *Gymnadenia conopsea*(L.) R.Br of the disclosure includes: (1) the root tuber of *Gymnadenia conopsea*(L.)R.Br is soaked in water so that it can be fully infiltrated until having been taken as a sample, no white core is observed in the root tuber of *Gymnadenia conopsea*(L.)R.Br.; (2) the root tuber of *Gymnadenia conopsea*(L.)R.Br is ultrafinely comminuted by wet method to obtain a dispersion slurry; (3) additional water is supplemented into the dispersion slurry to obtain diluted dispersion slurry followed by heating of the diluted dispersion slurry and adding neutral protease to the diluted dispersion slurry, and then extraction is carried out through circulation and homogenization by the homogenization pump to obtain extracted material fluid; (4) the extracted material fluid is treated through heat preservation and enzyme inactivation; (5) the extracted material fluid is subjected to coarse filtration to obtain a coarse filtrate; and (6) the coarse filtrate is subjected to fine filtration to obtain a fine filtrate. Therefore, The extracting method of the disclosure is unique and novel in process, and the extracted *Gymnadenia conopsea*(L.)R.Br extract has unique application value in the aspects of skin care, wound repair, anti-wrinkle, sunscreen, anti-oxidation, anti-allergy, skin moisturizing, etc., which has good application prospect in the field of cosmetics and is suitable for large-scale application.

2. The method for extracting *Gymnadenia conopsea*(L.)R.Br of the disclosure includes: (1) the root tuber of *Gymnadenia conopsea*(L.)R.Br is soaked in water so that it can be fully infiltrated until having been taken as a sample, no white core is observed in the root tuber of *Gymnadenia conopsea*(L.)R.Br.; (2) the root tuber of *Gymnadenia conopsea*(L.)R.Br is ultrafinely comminuted by wet method to obtain a dispersion slurry; (3) additional water is supplemented into the dispersion slurry to obtain diluted dispersion slurry followed by heating of the diluted dispersion slurry and adding neutral protease to the diluted dispersion slurry, and then extraction is carried out through circulation and homogenization by the homogenization pump to obtain extracted material fluid; (4) the extracted material fluid is treated through heat preservation and enzyme inactivation; (5) the extracted material fluid is subjected to coarse filtration to obtain a coarse filtrate; and (6) the coarse filtrate is subjected to fine filtration to obtain a fine filtrate. Therefore, the extracting method of the disclosure has the advantages of ingenious design, simple and convenient operation and low cost, and thus is suitable for large-scale application.

3. The extract of *Gymnadenia conopsea*(L.)R.Br according to the disclosure is prepared by the method for extracting *Gymnadenia conopsea*(L.)R.Br as above, and thus it has unique application value in the aspects of skin care, wound repair, anti-wrinkle, sunscreen, anti-oxidation, anti-allergy, skin moisturizing, etc., which has good application prospect in the field of cosmetics and is suitable for large-scale application.

4. The extract of *Gymnadenia conopsea*(L.)R.Br according to the disclosure is prepared by the method for extracting *Gymnadenia conopsea*(L.)R.Br as described above, the method has the advantages of ingenious design, simple and convenient operation and low cost, and thus is suitable for large-scale application.

These and other objects, features and advantages of the disclosure can be fully embodied by the following detailed description and claims, and can be realized by means, devices and their combinations specially pointed out in the attached claims.

DETAILED DESCRIPTION

Figure 1:
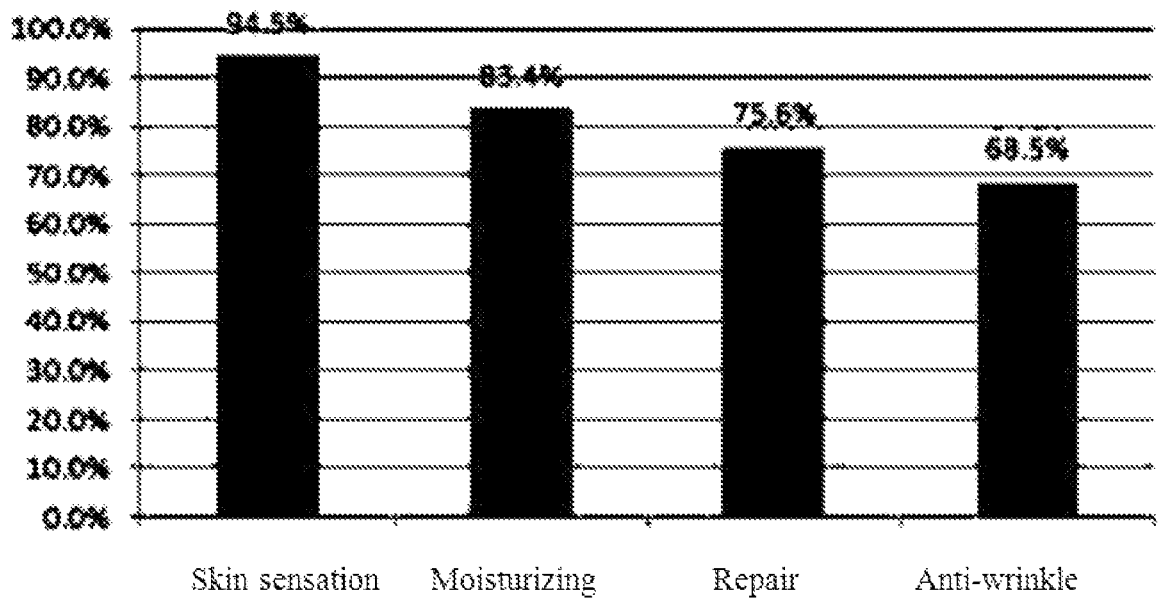
FIG. 1 is the statistical result of using effect score of *Gymnadenia conopsea*(L.)R.Br polysaccharide polysaccharide according to the disclosure.

In order to target extraction and/or purification of *Gymnadenia conopsea*(L.)R.Br polysaccharide, which is the most effective ingredient in *Gymnadenia conopsea*(L.)R.Br, and *Gymnadenia conopsea*(L.)R.Br polysaccharide complex, the inventor provides a method for extracting *Gymnadenia conopsea*(L.)R.Br, including the following steps:

(1) the root tuber of *Gymnadenia conopsea*(L.)R.Br is soaked in water so that it can be fully infiltrated until after having been taken as a sample, no white core is observed in the root tuber of *Gymnadenia conopsea*(L.)R.Br;

(2) the root tuber of *Gymnadenia conopsea*(L.)R.Br is ultrafinely comminuted by wet method to obtain a dispersion slurry;

(3) additional water is supplemented into the dispersion slurry to obtain diluted dispersion slurry followed by heating of the diluted dispersion slurry and adding neutral protease to the diluted dispersion slurry, and then extraction is carried out through circulation and homogenization by the homogenization pump to obtain extracted material fluid;

(4) the extracted material fluid is treated through heat preservation and enzyme inactivation;

(5) the extracted material fluid is subjected to coarse filtration to obtain a coarse filtrate; and (6) the coarse filtrate is subjected to fine filtration to obtain a fine filtrate.

In order to reduce the impurity, preferably before the step (1), the method for extracting *Gymnadenia conopsea*(L.)R.Br further includes the step of (a) washing the root tuber of *Gymnadenia conopsea*(L.)R.Br.

The washing can be performed by any suitable method, and preferably, the washing is a slow stirring washing of pure water.

In the step (1), the volume (by liter) of the water can be determined according to the need. In some embodiments, in the step (1), the volume (by liter) of water is 40-60 times of the weight (by kilogram) of the root tuber of *Gymnadenia conopsea*(L.)R.Br.

In the step (1), the temperature of the water can be determined according to the need. In some embodiments, in the step (1), the temperature of the water is kept at 40° C. to 60° C.

In the step (2), the ultrafine comminution by wet method can be carried out by any suitable equipment. In some embodiments, in the step (2), the ultrafine comminution by wet method is carried out by an ultra-fine crusher used for traditional Chinese medicine.

In the step (2), the particle size of the dispersion slurry can be determined according to the need. In some embodiments, in the step (2), the particle size of the dispersion slurry is 60 to 100 mesh.

In the step (3), the volume (by liter) of water contained in the diluted dispersion slurry can be determined according to the need. In some embodiments, in the step (3), the volume (by liter) of water contained in the diluted dispersion slurry is 40-100 times of the weight (by kilogram) of the root tuber of *Gymnadenia conopsea*(L.)R.Br.

In the step (3), the diluted dispersion slurry can be heated to any suitable temperature. In some embodiments, in the step (3), the diluted dispersion slurry is heated to 40° C. to 60° C.

In the step (3), the amount of the neutral protease added can be determined according to the need. In some embodiments, in the step (3), the neutral protease is added in an amount of 0.01% to 1.0% (by weight) relative to the weight of the root tuber of *Gymnadenia conopsea*(L.)R.Br.

In the step (3), the particle size of the extracted material fluid can be determined according to the need. In some embodiments, in the step (3), the particle size of the extracted material fluid should be 100 to 500 mesh.

In the step (3), the duration of extraction can be determined according to the need. In some embodiments, in the step (3), the duration of extraction is 1 to 6 hours.

In the step (4), the temperature and duration of heat preservation and enzyme inactivation can be determined according to the need. In some embodiments, in the step (4), the temperature of heat preservation and enzyme inactivation is 75° C. to 90° C., and the duration of heat preservation and enzyme inactivation is 15 to 30 minutes.

In the step (5), the coarse filtration can be carried out by any suitable method. In some embodiments, in the step (5), the coarse filtration is a pressure filtration by using a filter cloth with 400 to 1000 mesh and a medium speed filter paper.

In the step (6), the fine filtration can be carried out by any suitable method. In some embodiments, in the step (6), the fine filtration is carried out through a filter core with 0.2 to 0.45 μm.

To obtain the *Gymnadenia conopsea*(L.)R.Br polysaccharide and extract fluid of *Gymnadenia conopsea*(L.)R.Br, preferably, after the step (6), the method for extracting *Gymnadenia conopsea*(L.)R.Br further includes the following steps:
(71) the fine filtrate is concentrated to obtain a concentrated fluid;
(72) ethanol is added to the concentrated fluid for precipitation to obtain precipitate and supernatant;
(73) the precipitate is washed with the ethanol to obtain eluent, and then the precipitate is dried to obtain the *Gymnadenia conopsea*(L.)R.Br polysaccharide; and
(74) the supernatant is combined with the eluent followed by recovery under reduced pressure with dealcoholization, and butanediol is added thereto, thus transparent extract fluid of *Gymnadenia conopsea*(L.)R.Br is obtained.

In the step (71), the volume (by liter) of the concentrated fluid can be determined according to the need. More preferably, in the step (71), the volume (by liter) of the concentrated fluid is 10-40 times of the weight (by kilogram) of the root tuber of *Gymnadenia conopsea*(L.)R.Br.

In the step (72), the concentration of the ethanol can be determined according to the need. More preferably, in the step (72), the ethanol has a concentration of 70% (v/v) or more.

In the step (73), the drying can be carried out by any suitable drying manner. More preferably, in the step (73), the drying is freeze drying, vacuum drying or hot air circulation drying.

In the step (74), the amount of the butanediol added can be determined according to the need. More preferably, in the step (74), the butanediol is added in an amount of 5% to 50% by weight.

In order to obtain the extract fluid of *Gymnadenia conopsea*(L.)R.Br polysaccharide complex, preferably, after the step (6), the method for extracting *Gymnadenia conopsea* (L.)R.Br further includes the following steps:
(81) the fine filtrate is concentrated to obtain a concentrated fluid;
(82) the concentrated fluid is subjected to heat preservation and sterilization followed by a second fine filtration to obtain a second fine filtrate; and
(83) organic acids and/or diols are added into the second fine filtrate to obtain an extract fluid of *Gymnadenia conopsea*(L.)R.Br polysaccharide complex free of preservative.

In the step (81), the volume (by liter) of the concentrated fluid can be determined according to the need. More preferably, in the step (81), the volume (by liter) of the concentrated fluid is 10-40 times of the weight (by kilogram) of the root tuber of *Gymnadenia conopsea*(L.)R.Br.

In the step (82), the temperature and duration of heat preservation and sterilization can be determined according to the need. More preferably, in the step (82), the temperature of heat preservation and sterilization is 80° C. to 100° C., and the duration of heat preservation and sterilization is 15 to 30 minutes.

In the step (82), the second fine filtration can be carried out by any suitable method. More preferably, in the step (82), the second fine filtration is carried out through a filter core with 0.2 to 0.45 μm.

In the step (83), the specific species and amount of the organic acid added and the specific species and amount of the diols added can be determined according to the need. More preferably, in the step (83), the organic acid is p-anisic acid with an adding amount of 0.05% to 0.4% by weight, and the diol is propylene glycol with an adding amount of 5% to 30% by weight.

The disclosure also provides an extract of *Gymnadenia conopsea*(L.)R.Br, wherein the extract is prepared by the method for extracting *Gymnadenia conopsea*(L.)R.Br. as above.

The following Examples are described in detail in order to understand the technical content of the disclosure more clearly. The components or raw materials involved in the disclosure are conventional commercial products or can be obtained by conventional technical means in the art.

Example 1

(1) Washing:
The root tuber of *Gymnadenia conopsea*(L.)R.Br of 10 kg was placed into a 1000 L extraction tank, and then an appropriate amount of pure water was added to soak the root tuber of *Gymnadenia conopsea*(L.)R.Br Stirring had been carried out slowly with 10 rpm for 5 minutes. Then stirring was stopped and the washing water was discarded. The root tuber was washed repeatedly as above till the washing water was substantially clear, thus the washing was finished.
(2) Infiltrating:
The clean root tuber of *Gymnadenia conopsea*(L.)R.Br having been washed as above was added with pure water with a volume (by liter) of 40 times of the weight (by kilogram) of the root tuber of *Gymnadenia conopsea*(L.) R.Br, corresponding to 400 L of pure water here. Stirring was started followed by heating to 40° C. After the stirring was stopped, the root tuber of *Gymnadenia conopsea*(L.) R.Br was soaked overnight under heat preservation, so that it can be fully infiltrated till after having been taken as a sample, no white core was observed.
(3) Grinding:
The qualified root tuber of *Gymnadenia conopsea*(L.) R.Br after soaking was comminuted by using the crusher used for traditional Chinese medicine through wet method to obtain a dispersion slurry with the particle size of 60 mesh.
(4) Extracting:
An appropriate amount of pure water was added into the qualified dispersion slurry after grinding, in which particles of the root tuber were dispersed, to obtain the diluted dispersion slurry, so as to ensure the volume (by liter) of water in total contained in the diluted dispersion slurry being 40 times of the weight (by kilogram) of the root tuber of *Gymnadenia conopsea*(L.)R.Br, corresponding to 400 L of water here.

The diluted dispersion slurry was heated to 40° C., and then the neutral protease was added in an amount of 0.01% (by weight) relative to the weight of the root tuber of *Gymnadenia conopsea*(L.)R.Br After that, extraction was carried out for 1 hour through circulation and homogenization by the homogenization pump, to obtain extracted material fluid with the particle size of 100 mesh.

(5) Inactivating Enzyme:

After finishing the extraction, the extracted material fluid was heated to 75° C., the heat preservation and enzyme inactivation lasted for 30 minutes.

(6) Coarsely Filtrating:

The extracted material fluid was subjected to a pressure filtration by using a filter cloth with 400 mesh and a medium speed filter paper, to obtain a coarse filtrate which was substantially clear.

(7) Finely Filtrating:

The coarse filtrate was filtrated through a filter core with 0.45 μm to obtain a fine filtrate as a clear and transparent solution.

The *Gymnadenia conopsea*(L.)R.Br polysaccharide, extract fluid of *Gymnadenia conopsea*(L.)R.Br, and extract fluid of *Gymnadenia conopsea*(L.)R.Br polysaccharide complex were prepared as follow, respectively:

(i) *Gymnadenia conopsea*(L.)R.Br polysaccharide, extract fluid of *Gymnadenia conopsea*(L.)R.Br:

concentrating: The above fine filtrate was subjected to concentration under reduced pressure to achieve a volume (by liter) being 10 times of the weight (by kilogram) of the root tuber of *Gymnadenia conopsea*(L.)R.Br, corresponding to 100 L of the fine filtrate here; in this case, the concentration was stopped and the concentrated fluid was obtained.

precipitating: The concentrated fluid was added with ethanol having a concentration of 70% (v/v), and stirred to allow for precipitation until the precipitation was complete.

drying: The precipitate was taken while retaining the supernatant, and then the precipitate was pressed to dryness followed by being washed with ethanol having a concentration of 70% (v/v) again. The eluent was collected, and the precipitate was pressed to dryness. The above operations were repeated 2-3 times to remove the alcohol-soluble impurities in the precipitate. The precipitate was pressed to dryness to obtain the *Gymnadenia conopsea*(L.)R.Br polysaccharide as a wet solid. The wet solid was dried in a hot-air circulation oven (or vacuum drying oven or freeze dryer) to constant weight to obtain a nearly white solid, namely, the *Gymnadenia conopsea*(L.)R.Br polysaccharide (product 1).

The supernatant was combined with the eluent followed by recovery under reduced pressure with dealcoholize so as to obtain a liquid concentrate free of ethanol but rich in functional substances, such as small molecular *Gymnadenia conopsea*(L.)R.Br, polysaccharides, *Gymnadenia conopsea*(L.)R.Br saponins and other glycosides, gastrodin, and trace elements. Then, the liquid concentrate was added with butanediol of 50% by weight to obtain an extract fluid of *Gymnadenia conopsea*(L.)R.Br (product 2).

(ii) extract fluid of *Gymnadenia conopsea*(L.)R.Br polysaccharide complex:

The above fine filtrate was concentrated under reduced pressure to achieve a volume (by liter) being 10 times of the weight (by kilogram) of the root tuber of *Gymnadenia conopsea*(L.)R.Br, corresponding to 100 L of the filtrate here. After the concentration was completed, a kind of extract fluid of *Gymnadenia conopsea*(L.)R.Br polysaccharide complex of total components was obtained with specific viscosity and polysaccharide content.

The above extract fluid of *Gymnadenia conopsea*(L.)R.Br polysaccharide complex of total components was heated to 80° C. followed by heat preservation and sterilization for 30 minutes, and subjected to a second fine filtration through a filter core with 0.3 μm, to obtain a second fine filtrate which was a clear and transparent solution.

The above second fine filtrate was added with p-anisic acid (that was an organic acid) with the amount of 0.4% by weight, to prepare extract fluid of *Gymnadenia conopsea*(L.)R.Br polysaccharide complex free of preservative (product 3).

The characteristic indexes of *Gymnadenia conopsea*(L.)R.Br polysaccharide (product 1) were as follows:

| Test items | standard | test results |
| --- | --- | --- |
| Properties and state | light white powder | accordant |
| Odor | slightly characteristic odor of Gymnadenia conopsea(L.)R.Br or odorless | accordant |
| Viscosity (1.0% aqueous solution, 20° C.) | 1000-3000 cp | 1500 cp |
| pH (0.5% aqueous solution) | 5.0-7.0 | 6.47 |
| Total polysaccharide content (phenol-sulfuric acid method) | ≥50% | 87.6% |
| Nitrogen content | ≤0.5% | 0.38 |
| Molecular weight (HPLC method) | ≥100,000 daltons | 160,000 daltons |

The characteristic indexes of the extract fluid of *Gymnadenia conopsea*(L.)R.Br. (product 2) were as follows:

| Test items | standard | test results |
| --- | --- | --- |
| Properties and state | light yellow transparent liquid | accordant |
| Odor | slightly characteristic odor of Gymnadenia conopsea(L.)R.Br | accordant |
| pH (diluted to 5 times) | 5.0-7.0 | 6.21 |
| Dry matter content | ≥0.5% | 0.72 |
| Total nitrogen content | ≤5.0% | 4.2 |
| aminophenol content | 1.0-5.0% | 2.6 |

The characteristic indexes of the extract fluid of *Gymnadenia conopsea*(L.)R.Br. polysaccharide complex (product 3) were as follows:

| Test items | standard | test results |
| --- | --- | --- |
| Properties and state | light yellow transparent viscous liquid | accordant |
| Odor | slightly characteristic odor of Gymnadenia conopsea(L.)R.Br. | accordant |

-continued

| Test items | standard | test results |
| --- | --- | --- |
| Viscosity (20° C.) | 500-5000 cp | 4500 |
| pH (diluted to 5 times) | 5.0-7.0 | 6.18 |
| Dry matter content | ≥0.5% | 4.8 |
| Total nitrogen content | ≤5.0% | 3.42 |
| aminophenol content | 1.0-5.0% | 2.26 |

Example 2

(1) Washing:

The root tuber of Gymnadenia conopsea(L.)R.Br of 10 kg was placed into a 1000 L extraction tank, and then an appropriate amount of pure water was added to soak the root tuber of Gymnadenia conopsea(L.)R.Br Stirring had been carried out slowly with 50 rpm for 5 minutes. Then stirring was stopped and the washing water was discarded. The root tuber was washed repeatedly as above till the washing water was substantially clear, thus the washing was finished.

(2) Infiltrating:

The clean root tuber of Gymnadenia conopsea(L.)R.Br having been washed as above was added with pure water with a volume (by liter) of 50 times of the weight (by kilogram) of the root tuber of Gymnadenia conopsea(L.)R.Br, corresponding to 500 L of pure water here. Stirring was started followed by heating to 50° C. After the stirring was stopped, the root tuber of Gymnadenia conopsea(L.)R.Br was soaked for 8 hours or more under heat preservation, so that it can be fully infiltrated till after having been taken as a sample, no white core was observed.

(3) Grinding:

The qualified root tuber of Gymnadenia conopsea(L.)R.Br after soaking was comminuted by using the crusher used for traditional Chinese medicine through wet method to obtain a dispersion slurry with the particle size of 80 mesh.

(4) Extracting:

An appropriate amount of pure water was added into the qualified dispersion slurry after grinding, to obtain the diluted dispersion, so as to ensure the volume (by liter) of water in total contained in the diluted dispersion being 60 times of the weight (by kilogram) of the root tuber of Gymnadenia conopsea(L.)R.Br, corresponding to 600 L of water here.

The diluted dispersion was heated to 50° C., and then the neutral protease was added in an amount of 0.5% (by weight) relative to the weight of the root tuber of Gymnadenia conopsea(L.)R.Br After that, extraction was carried out for 3 hours through circulation and homogenization by the homogenization pump, to obtain extracted material fluid with the particle size of 300 mesh.

(5) Inactivating Enzyme:

After finishing the extraction, the extracted material fluid was heated to 80° C., the heat preservation and enzyme inactivation lasted for 20 minutes.

(6) Coarsely Filtrating:

The extracted material fluid was subjected to a pressure filtration by using a filter cloth with 600 mesh and a medium speed filter paper, to obtain a coarse filtrate which was substantially clear.

(7) Finely Filtrating:

The coarse filtrate was filtrated through a filter core with 0.3 μm to obtain a fine filtrate as a clear and transparent solution.

The Gymnadenia conopsea(L.)R.Br polysaccharide, extract fluid of Gymnadenia conopsea(L.)R.Br, and extract fluid of Gymnadenia conopsea(L.)R.Br polysaccharide complex were prepared as follow, respectively:

(i) Gymnadenia conopsea(L.)R.Br polysaccharide, extract fluid of Gymnadenia conopsea(L.)R.Br.:

concentrating: The above fine filtrate was subjected to concentration under reduced pressure to achieve a volume (by liter) being 20 times of the weight (by kilogram) of the root tuber of Gymnadenia conopsea(L.)R.Br, corresponding to 200 L of the fine filtrate here; in this case, the concentration was stopped and the concentrated fluid was obtained.

precipitating: The concentrated fluid was added with ethanol having a concentration of 80% (v/v), and stirred to allow for precipitation until the precipitation was complete.

drying: The precipitate was taken while retaining the supernatant, and then the precipitate was pressed to dryness followed by being washed with ethanol having a concentration of 80% (v/v) again. The eluent was collected, and the precipitate was pressed to dryness. The above operations were repeated 2-3 times to remove the alcohol-soluble impurities in the precipitate. The precipitate was pressed to dryness to obtain the Gymnadenia conopsea(L.)R.Br polysaccharide as a wet solid. The wet solid was dried in a hot-air circulation oven (or vacuum drying oven or freeze dryer) to constant weight to obtain a nearly white solid, namely, the Gymnadenia conopsea(L.)R.Br polysaccharide (product 4).

The supernatant was combined with the eluent followed by recovery under reduced pressure with dealcoholize so as to obtain a liquid concentrate free of ethanol but rich in functional substances, such as small molecular Gymnadenia conopsea(L.)R.Br polysaccharides, Gymnadenia conopsea(L.)R.Br saponins and other glycosides, gastrodin, and trace elements. Then, the liquid concentrate was added with butanediol of 30% by weight to obtain a transparent extract fluid of Gymnadenia conopsea(L.)R.Br (product 5).

(ii) extract fluid of Gymnadenia conopsea(L.)R.Br polysaccharide complex:

The above fine filtrate was concentrated under reduced pressure to achieve a volume (by liter) being 20 times of the weight (by kilogram) of the root tuber of Gymnadenia conopsea(L.)R.Br, corresponding to 200 L of the filtrate here. After the concentration was completed, a kind of extract fluid of Gymnadenia conopsea(L.)R.Br polysaccharide complex of total components was obtained with specific viscosity and polysaccharide content.

The above extract fluid of Gymnadenia conopsea(L.)R.Br polysaccharide complex of total components was heated to 90° C. followed by heat preservation and sterilization for 20 minutes, and subjected to a second fine filtration through a filter core with 0.45 μm to obtain a second fine filtrate which was a clear and transparent solution.

The above second fine filtrate was added with p-anisic acid (that was an organic acid) with the amount of 0.2% by weight, to prepare extract fluid of Gymnadenia conopsea(L.)R.Br polysaccharide complex free of preservative (product 6).

The characteristic indexes of *Gymnadenia conopsea*(L.) R.Br polysaccharide (product 4) were as follows:

| Test items | standard | test results |
|---|---|---|
| Properties and state | light white powder | accordant |
| Odor | slightly characteristic odor of Gymnadenia conopsea(L.)R.Br. or odorless | accordant |
| Viscosity (1.0% aqueous solution, 20° C.) | 1000-3000 cp | 1800 cp |
| pH (0.5% aqueous solution) | 5.0-7.0 | 6.21 |
| Total polysaccharide content (phenol-sulfuric acid method) | ≥50% | 90.2% |
| Nitrogen content | ≤0.5% | 0.24 |
| Molecular weight (HPLC method) | ≥100,000 daltons | 450,000 daltons |

The characteristic indexes of the extract fluid of *Gymnadenia conopsea*(L.)R.Br (product 5) were as follows:

| Test items | standard | test results |
|---|---|---|
| Properties and state | light yellow transparent liquid | accordant |
| Odor | slightly characteristic odor of Gymnadenia conopsea(L.)R.Br. | accordant |
| pH (diluted to 5 times) | 5.0-7.0 | 6.38 |
| Dry matter content | ≥0.5% | 0.96 |
| Total nitrogen content | ≤5.0% | 3.81 |
| aminophenol content | 1.0~5.0% | 2.42 |

The characteristic indexes of extract fluid of *Gymnadenia conopsea*(L.)R.Br polysaccharide complex (product 6) were as follows:

| Test items | standard | test results |
|---|---|---|
| Properties and state | light yellow transparent viscous liquid | accordant |
| Odor | slightly characteristic odor of Gymnadenia conopsea(L.)R.Br. | accordant |
| Viscosity (20° C.) | 500-5000 cp | 3100 |
| pH (diluted to 5 times) | 5.0-7.0 | 6.42 |
| Dry matter content | ≥0.5% | 2.65 |
| Total nitrogen content | ≤5.0% | 3.15 |
| aminophenol content | 1.0-5.0% | 2.04 |

Example 3

(1) Washing:

The root tuber of *Gymnadenia conopsea*(L.)R.Br of 10 kg was placed into a 1000 L extraction tank, and then an appropriate amount of pure water was added to soak the root tuber of *Gymnadenia conopsea*(L.)R.Br Stirring had been carried out slowly with 20 rpm for 5 minutes. Then, stirring was stopped and the washing water was discarded. The root tuber was washed repeatedly as above until the washing water was substantially clear, thus the washing was finished.

(2) Infiltrating:

The clean root tuber of *Gymnadenia conopsea*(L.)R.Br having been washed as above was added with pure water with a volume (by liter) of 60 times of the weight (by kilogram) of the root tuber of *Gymnadenia conopsea*(L.) R.Br, corresponding to 600 L of pure water here. Stirring was started followed by heating to 60° C. After the stirring was stopped, the root tuber of *Gymnadenia conopsea*(L.) R.Br was soaked overnight under heat preservation, so that it can be fully infiltrated till after having been taken as a sample, no white core was observed.

(3) Grinding:

The qualified root tuber of *Gymnadenia conopsea*(L.) R.Br after soaking was comminuted by using the crusher used for traditional Chinese medicine through wet method to obtain a dispersion slurry with the particle size of 100 mesh.

(4) Extracting:

An appropriate amount of pure water was added into the qualified dispersion slurry after grinding, in which particles of the root tuber were dispersed, to obtain the diluted dispersion, so as to ensure the volume (by liter) of water in total contained in the diluted dispersion being 100 times of the weight (by kilogram) of the root tuber of *Gymnadenia conopsea*(L.)R.Br, corresponding to 1000 L of water here.

The diluted dispersion was heated to 60° C., and then the neutral protease was added in an amount of 1.0% (by weight) relative to the weight of the root tuber of *Gymnadenia conopsea*(L.)R.Br. After that, extraction was carried out for 6 hour through circulation and homogenization by the homogenization pump, to obtain extracted material fluid with the particle size of 500 mesh.

(5) Inactivating Enzyme:

After finishing the extraction, the extracted material fluid was heated to 90° C., the heat preservation and enzyme inactivation lasted for 15 minutes.

(6) Coarsely Filtrating:

The extracted material fluid was subjected to a pressure filtration by using a filter cloth with 1000 mesh and a medium speed filter paper, to obtain a coarse filtrate which was substantially clear.

(7) Finely Filtrating:

The coarse filtrate was filtrated through a filter core with 0.2 μm to obtain a fine filtrate as a clear and transparent solution.

*Gymnadenia conopsea*(L.)R.Br polysaccharide, extract of *Gymnadenia conopsea*(L.)R.Br, and extract of *Gymnadenia conopsea*(L.)R.Br polysaccharide complex were prepared as follow, respectively:

(i) *Gymnadenia conopsea*(L.)R.Br polysaccharide, extract fluid of *Gymnadenia conopsea*(L.)R.Br.:

concentrating: The above fine filtrate was subjected to concentration under reduced pressure to achieve a volume (by liter) being 40 times of the weight (by kilogram) of the root tuber of *Gymnadenia conopsea* (L.)R.Br, corresponding to 400 L of the fine filtrate here; in this case, the concentration was stopped and the concentrated fluid was obtained.

precipitating: The concentrated fluid was added with ethanol having a concentration of 95% (v/v), and the resultant was stirred to allow for precipitation until the precipitation was complete.

drying: The precipitate was taken while retaining the supernatant, and then the precipitate was pressed to dryness followed by being washed with ethanol having a concentration of 95% (v/v) again. The eluent was collected, and the precipitate was pressed to dryness. The above operations were repeated 2-3 times to remove the alcohol-soluble impurities in the precipitate. The precipitate was pressed to dryness to obtain the *Gymnadenia conopsea*(L.)R.Br polysaccharide as a wet solid. The wet solid was dried in a hot-air circulation oven (or vacuum drying oven or freeze dryer) to constant weight to obtain a nearly white solid, namely, the *Gymnadenia conopsea*(L.) R.Br polysaccharide (product 7).

The supernatant was combined with the eluent followed by recovery under reduced pressure with dealcoholize so as to obtain a liquid concentrate free of ethanol but rich in functional substances, such as small molecular *Gymnadenia conopsea*(L.)R.Br polysaccharides, *Gymnadenia conopsea* (L.)R.Br saponins and other glycosides, gastrodin, and trace elements. Then, the liquid concentrate was added with butanediol of 5% by weight to obtain a transparent extract fluid of *Gymnadenia conopsea*(L.)R.Br (product 8).

(ii) extract fluid of *Gymnadenia conopsea*(L.)R.Br polysaccharide complex:

The above fine filtrate was concentrated under reduced pressure to achieve a volume (by liter) being 40 times of the weight (by kilogram) of the root tuber of *Gymnadenia conopsea*(L.)R.Br, corresponding to 400 L of the filtrate here. After the concentration was completed, a kind of extract fluid of *Gymnadenia conopsea*(L.)R.Br polysaccharide complex of total components was obtained with specific viscosity and polysaccharide content.

The above extract fluid of *Gymnadenia conopsea*(L.) R.Br polysaccharide complex of total components was heated to 100° C. followed by heat preservation and sterilization for 15 minutes, and subjected to a second fine filtration through a filter core with 0.2 μm to obtain a second fine filtrate which was a clear and transparent solution.

The above second fine filtrate was added with p-anisic acid (that was an organic acid) with the amount of 0.05% by weight, to prepare extract fluid of *Gymnadenia conopsea*(L.)R.Br polysaccharide complex free of preservative (product 9).

The characteristic indexes of *Gymnadenia conopsea*(L.) R.Br polysaccharide (product 7) were as follows:

| Test items | standard | test results |
| --- | --- | --- |
| Properties and state | light white powder | accordant |
| Odor | slightly characteristic odor of Gymnadenia conopsea(L.)R.Br. or odorless | accordant |
| Viscosity (1.0% aqueous solution, 20° C.) | 1000-3000 cp | 2700 cp |
| pH (0.5% aqueous solution) | 5.0-7.0 | 6.02 |
| Total polysaccharide content (phenol-sulfuric acid method) | ≥50% | 94.3% |
| Nitrogen content | ≤0.5% | 0.08 |
| Molecular weight (HPLC method) | ≥100,000 daltons | 870,000 daltons |

The characteristic indexes of the extract fluid of *Gymnadenia conopsea*(L.)R.Br. (product 8) were as follows:

| Test items | standard | test results |
| --- | --- | --- |
| Properties and state | light yellow transparent liquid | accordant |
| Odor | slightly characteristic odor of Gymnadenia conopsea(L.)R.Br | accordant |
| pH (diluted to 5 times) | 5.0-7.0 | 6.72 |
| Dry matter content | ≥0.5% | 0.87 |
| Total nitrogen content | ≤5.0% | 3.88 |
| aminophenol content | 1.0-5.0% | 2.14 |

The characteristic indexes of extract fluid of *Gymnadenia conopsea*(L.)R.Br polysaccharide complex (product 9) were as follows:

| Test items | standard | test results |
| --- | --- | --- |
| Properties and state | light yellow transparent viscous liquid | accordant |
| Odor | slightly characteristic odor of Gymnadenia conopsea(L.)R.Br. | accordant |
| Viscosity (20° C.) | 500-5000 cp | 870 |
| pH (diluted to 5 times) | 5.0-7.0 | 6.18 |
| Dry matter content | ≥0.5% | 1.02 |
| Total nitrogen content | ≤5.0% | 3.21 |
| aminophenol content | 1.0-5.0% | 1.09 |

Example 4

Experimental Products:

The above product 1, product 4, and product 7 were mixed with glycerol of 5% (v/v) and water, respectively, and then the conventional preservative comprising phenoxy alcohol of 0.6% (v/v) and capryl glycol of 0.1% (v/v) were added to produce essence fluid of 0.3% by weight (that is, product 1, product 4, and product 7 were contained in a content of 0.3% by weight)

Experimental Subjects:

There were 33 volunteers aged 24-56 years old, who suffered the main skin problems such as acne, slight external skin damage, dry itching and peeling, fine lines, wrinkles, slack and so on.

Experimental Process:

The above volunteers were divided into 3 groups on average, 11 in each group. Each group was asked to apply the essence fluid containing product 1, product 4, or product 7 once every morning and evening, with about 0.5 ml each time on the face skin evenly for 28 days. The improvement of skin was observed, and the questionnaire was filled and scored.

| efficacy | 5-point | 4-point | 3-point | 2-point | 1-point |
| --- | --- | --- | --- | --- | --- |
| Skin sensation | excellent smoothness | obvious smoothness | middling smoothness | slight smoothness | no smoothness |
| Moisturizing | excellent sense of moisture | obvious sense of moisture | moderate sense of moisture | slight sense of moisture | no feeling |

| efficacy | 5-point | 4-point | 3-point | 2-point | 1-point |
| --- | --- | --- | --- | --- | --- |
| Repair | complete repair | obvious improvement | moderate efficacy | slight repair | no efficacy |
| Anti-wrinkle | obviously reducing the wrinkle with increased skin elasticity | weakening the wrinkle with slight skin firmness | moderate efficacy | slight efficacy | no efficacy |

Experimental Result:

The three groups were the same with regard to the scoring results, the statistical results of scoring were shown in FIG. 1. The experimental results showed that the *Gymnadenia conopsea*(L.)R.Br polysaccharide can allow the product to have excellent skin sensation with the moisturizing degree of 83.4%, as well as good repair and anti-wrinkle effects with the repair rate of 75.6% and the anti-wrinkle effect of 68.5%.

Example 5

Experimental Products:

The above product 2, product 5, and product 8 were mixed with glycerol of 5% (v/v) and water and xanthan gum of 0.4% (v/v), respectively, and then the conventional preservative comprising phenoxy alcohol of 0.6% (v/v) and capryl glycol of 0.1% (v/v) were added to produce essence fluid of 2.0% by weight (that is, product 2, product 5, and product 8 were contained in a content of 2.0% by weight).

Experimental Subjects:

There were 18 volunteers aged 27-43 years old, who suffered the main skin problems such as inflammation, acne, red blood silk, chloasma, redness and swelling and so on.

Experimental Process:

The above volunteers were divided into 3 groups on average, 6 in each group. Each group was asked to apply the essence fluid containing product 2, product 5, or product 8 once every morning and evening, with about 0.5 ml each time on the face skin evenly for 28 days. The improvement of skin was observed, and the questionnaire was filled and scored.

Figure 2:
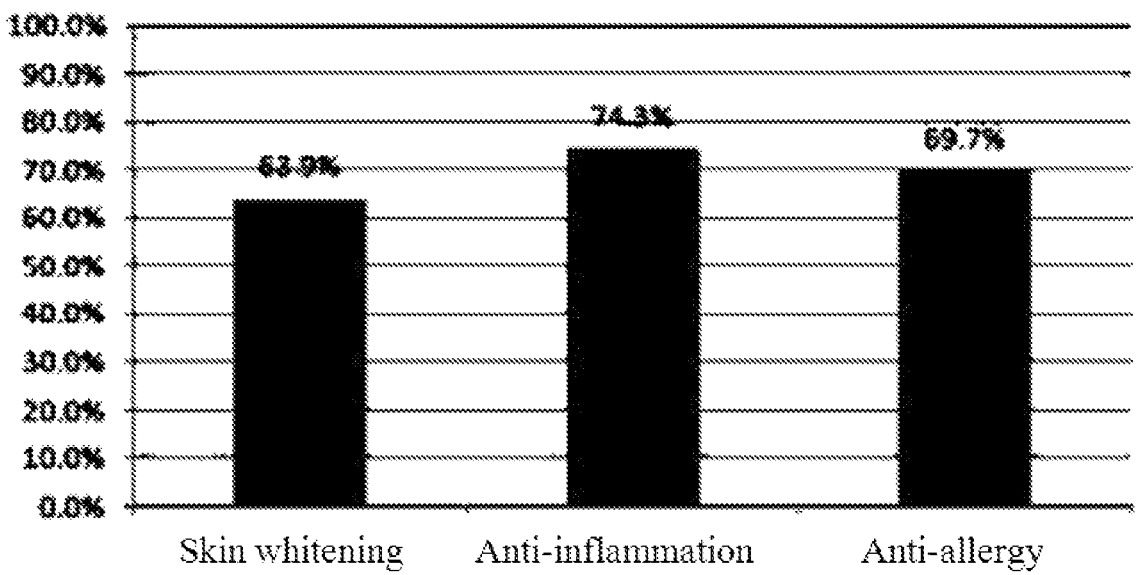
FIG. 2 is the statistical result of using effect score of extract fluid of *Gymnadenia conopsea*(L.)R.Br polysaccharide according to the disclosure.

Experimental Result:

The three groups were the same with regard to the scoring results, the statistical results of scoring were shown in FIG. 2. The experimental results showed that the extract fluid product of *Gymnadenia conopsea*(L.)R.Br polysaccharide has excellent skin whitening, anti-inflammation, and anti-allergy effects, with the skin whitening effect of 63.9%, anti-inflammation effect of 74.3%, and anti-allergy effect of 69.7%.

Example 6

Experimental Products:

The above product 3, product 6, and product 9 were mixed with glycerol of 5% (v/v) and water respectively, and then the conventional preservative comprising phenoxy alcohol of 0.6% (v/v) and capryl glycol of 0.1% (v/v) were added to produce essence fluid of 2.0% by weight (that is, product 3, product 6, and product 9 were contained in a content of 2.0% by weight).

Experimental Subjects:

There were 72 volunteers aged 21-64 years old, who suffered the main skin problems such as acne, slight external skin damage, dry itching and peeling, fine lines, wrinkles, slack and so on.

Experimental Process:

The above volunteers were divided into 3 groups on average, 24 in each group. Each group was asked to apply the essence fluid containing product 3, product 6, or product 9 once every morning and evening, with about 0.5 ml each time on the face skin evenly for 28 days. The improvement of skin was observed, and the questionnaire was filled and scored.

| efficacy | 5-point | 4-point | 3-point | 2-point | 1-point |
| --- | --- | --- | --- | --- | --- |
| Skin whitening | disappearance of color spots | obvious fading of color spots | slight fading of color spots | slight improvement in skin color | no improvement |
| Anti-inflammation | complete disappearance of inflammation | obvious improvement in inflammation | slight improvement in inflammation | slight improvement | no improvement |
| Anti-allergy | Complete disappearance of the red area | obvious improvement | slight improvement | no tingling sensation | no efficacy |

| efficacy | 5-point | 4-point | 3-point | 2-point | 1-point |
|---|---|---|---|---|---|
| Skin sensation | Excellent smoothness | obvious smoothness | middling smoothness | slight smoothness | no smoothness |
| Moisturizing | excellent sense of moisture | obvious sense of moisture | moderate sense of moisture | slight sense of moisture | no feeling |
| Repair | complete repair | obvious improvement | moderate efficacy | slight repair | no efficacy |
| Anti-wrinkle | obviously reducing the wrinkle with increased skin elasticity | weakening the wrinkle with slight skin firmness | moderate efficacy | slight efficacy | no efficacy |
| Skin whitening | disappearance of color spots | obvious fading of color spots | slight fading of color spots | slight improvement in skin color | no improvement |
| Anti-inflammation | complete disappearance of inflammation | obvious improvement in inflammation | slight improvement in inflammation | slight improvement | no improvement |
| Anti-allergy | complete disappearance of the red area | obvious improvement | slight improvement | no tingling sensation | no efficacy |

Figure 3:
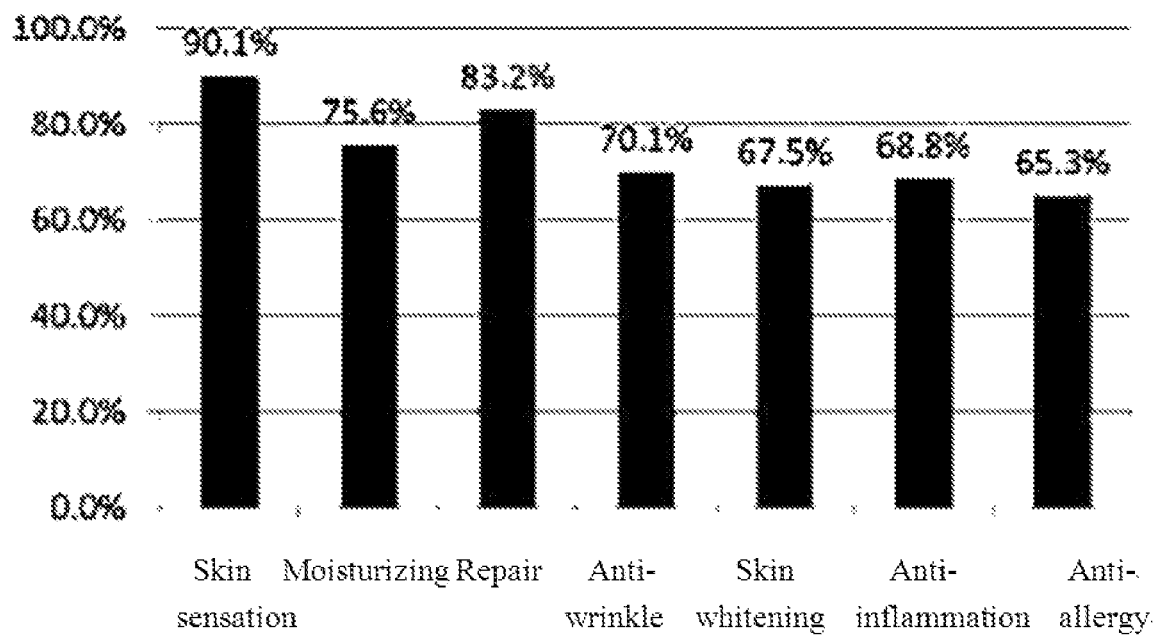
FIG. 3 is the statistical result of using effect score of extract fluid *Gymnadenia conopsea*(L.)R.Br polysaccharide complex according to the disclosure.

Experimental Result:

The three groups were the same with regard to the scoring results, the statistical results of scoring were shown in FIG. 3. The results showed that the extract fluid of *Gymnadenia conopsea*(L.)R.Br polysaccharide complex can allow the product to have excellent skin sensation, as well as comprehensive skin care effect.

Therefore, the skin care product added with the above products 1-9 has excellent skin smoothness, as well as good anti-allergy, anti-inflammation, skin whitening, moisturizing, repair, and anti-wrinkle effects, mainly applied in a dosage form of facial mask, aqueous agent, cream, lotion, etc. In addition, in the step of the last stage of Examples 1 to 3, the second fine filtrate is added with propylene glycol having a concentrations of 30%, 20%, and 5% by weight respectively, so as to prepare 3 extract fluids of *Gymnadenia conopsea*(L.)R.Br polysaccharide complex free of preservative, which have the similar effect to that of Example 6.

Accordingly, the disclosure provides method for preparing *Gymnadenia conopsea*(L.)R.Br polysaccharide, extract fluid of *Gymnadenia conopsea*(L.)R.Br, and extract fluid of *Gymnadenia conopsea*(L.)R.Br polysaccharide complex, which can be applied in the field of cosmetics and are suitable for industrial production without using dangerous organic solvents.

The method for extracting *Gymnadenia conopsea*(L.)R.Br according to the disclosure is unique and novel, in which tissue cells are broken by the physical breaking method so that the dissolving of effective substances can be promoted, thus the yield of the product are greatly increased; in the other hand, tissue protein is decomposed into small molecule active peptide and amino acid-based substance by protease to eliminate allergen, ensuring its safety and unique application value in the aspects of skin care, wound repair, anti-wrinkle, sunscreen, anti-oxidation, anti-allergy and skin moisturizing. The extract of *Gymnadenia conopsea*(L.)R.Br obtained through such process has good application prospect in the field of cosmetics.

The method of the disclosure has the advantages of ingenious design, simple and convenient operation and reasonable process, and the product obtained by this method has high yield and purity, thus achieving the purpose of maximizing the output value and maximizing the social and economic value of *Gymnadenia conopsea*(L.)R.Br.

The *Gymnadenia conopsea*(L.)R.Br polysaccharide, extract fluid of *Gymnadenia conopsea*(L.)R.Br polysaccharide, and extract fluid of *Gymnadenia conopsea*(L.)R.Br polysaccharide complex obtained according to the disclosure have unique application values in the aspects of skin care, wound repair, anti-wrinkle, sunscreen, anti-oxidation, anti-allergy, skin moisturizing and so on, which have good application prospect in the field of cosmetics. Instead, at present, there are few reports on the application of *Gymnadenia conopsea*(L.)R.Br in cosmetics.

To sum up, the method for extracting *Gymnadenia conopsea*(L.)R.Br according to the disclosure is unique and novel, and the extract of *Gymnadenia conopsea*(L.)R.Br thus obtained has unique application values in the aspects of skin care, wound repair, anti-wrinkle, sunscreen, anti-oxidation, anti-allergy and skin moisturizing, which has good application prospect in the field of cosmetics. The method of the disclosure has the advantages of ingenious design, simple and convenient operation and low cost and is suitable for large-scale application.

It can be seen that the objects of the disclosure have been completely and effectively realized. The disclosure has shown and explained its function and structural principle in the Examples, to which any modification can be made without departing from the principle. Therefore, the disclosure includes all variant embodiments based on the spirit and scope of the claims.

What is claimed is:

1. A method for extracting *Gymnadenia conopsea*(L.)R.Br., wherein the method comprises the following steps:
    (1) the root tuber of *Gymnadenia conopsea*(L.)R.Br. is soaked in water so that it can be fully infiltrated until being taken as a sample, wherein no white core is observed in the root tuber of *Gymnadenia conopsea*(L.)R.Br.;
    (2) the soaked root tuber of *Gymnadenia conopsea*(L.)R.Br. is ultrafinely comminuted by wet method to obtain a dispersion slurry;
    (3) additional water is supplemented into the dispersion slurry to obtain a diluted dispersion followed by heating of the diluted dispersion and adding neutral protease to the diluted dispersion, and then extraction is carried out through circulation and homogenization with a homogenization pump in order to obtain extracted material fluid;

(4) the extracted material fluid is treated through heat preservation and enzyme inactivation;

(5) the extracted material fluid is subjected to coarse filtration to obtain a coarse filtrate; and (6) the coarse filtrate is subjected to fine filtration in order to obtain a fine filtrate.

2. The method for extracting *Gymnadenia conopsea*(L.) R.Br. as claimed in claim 1, wherein in the step (1), the volume (by liter) of water is 40-60 times of the weight (by kilogram) of the root tuber of *Gymnadenia conopsea*(L.) R.Br.; or, the temperature of the water is kept between 40° C. and 60° C.

3. The method for extracting *Gymnadenia conopsea*(L.) R.Br. as claimed in claim 1, wherein in the step (2), the ultrafine comminution by wet method is carried out by an ultra-fine crusher used for wet method of traditional Chinese medicine; or, the particle size of the dispersion slurry is 60 to 100 mesh.

4. The method for extracting *Gymnadenia conopsea*(L.) R.Br. as claimed in claim 1, wherein in the step (3), the volume (by liter) of water contained in the diluted dispersion is 40-100 times of the weight (by kilogram) of the root tuber of *Gymnadenia conopsea*(L.)R.Br.; or, the diluted dispersion is heated to 40° C. to 60° C.; or, the neutral protease is added in an amount of 0.01% to 1.0% (by weight) relative to the weight of the root tuber of *Gymnadenia conopsea*(L.)R.Br.; or, the extracted material fluid has the particle size of 100 to 500 mesh; or the duration of extraction is 1 to 6 hours.

5. The method for extracting *Gymnadenia conopsea*(L.) R.Br. as claimed in claim 1, wherein in the step (4), the temperature of heat preservation and enzyme inactivation is 75° C. to 90° C., and the duration of heat preservation and enzyme inactivation is 15 to 30 minutes; or, in step (5), the coarse filtration is a pressure filtration by using a filter cloth with 400 to 1000 mesh and a medium speed filter paper; or, in step (6), the fine filtration is carried out through a filter core with 0.2 to 0.45 μm.

6. The method for extracting *Gymnadenia conopsea*(L.) R.Br. as claimed in claim 1, wherein after the step (6), the extraction method further includes the following steps:

(7-1) the fine filtrate is concentrated to obtain a concentrated fluid;

(7-2) ethanol is added in the concentrated fluid to obtain a precipitate and a supernatant;

(7-3) the precipitate is washed with ethanol to obtain an eluent, and then the precipitate is dried to obtain *Gymnadenia conopsea*(L.)R.Br. polysaccharide; and (7-4) the supernatant is combined with the eluent followed by recovery under reduced pressure with dealcoholize, and butanediol is added thereto, whereby an extract fluid of *Gymnadenia conopsea*(L.)R.Br. is obtained.

7. The method for extracting *Gymnadenia conopsea*(L.) R.Br. as claimed in claim 6, wherein in the step (7-1), the volume (by liter) of the concentrated fluid is 10-40 times of the weight (by kilogram) of the root tuber of *Gymnadenia conopsea*(L.)R.Br.; or, in the step (7-2), the ethanol has a concentration of 70% (v/v) or more; or, in the step (7-3), the drying is freeze drying, vacuum drying or hot air circulation drying; or, in the step (7-4), the butanediol is added in an amount of 5% to 50% by weight.

8. The method for extracting *Gymnadenia conopsea*(L.) R.Br. as claimed in claim 1, wherein after the step (6), the method further includes the following steps:

(8-1) the fine filtrate is concentrated to obtain a concentrated fluid;

(8-2) the concentrated fluid is subjected to heat preservation and sterilization followed by a second fine filtration to obtain a second fine filtrate; and (8-3) organic acids and/or diols are added into the second fine filtrate in order to obtain an extract fluid of *Gymnadenia conopsea*(L.)R.Br. polysaccharide complex free of preservative.

9. The method for extracting *Gymnadenia conopsea*(L.) R.Br. as claimed in claim 8, wherein in that in the step (8-1), the volume (by liter) of the concentrated fluid is 10-40 times of the weight (by kilogram) of the root tuber of *Gymnadenia conopsea*(L.)R.Br.; or, in the step (8-2), the temperature of heat preservation and sterilization is 80° C. to 100° C., and the duration of heat preservation and sterilization is 15 to 30 minutes; or, the second fine filtration is carried out through a filter core with 0.2 to 0.45 μm; or, in the step (8-3), the organic acid is p-anisic acid in an amount of 0.05% to 0.4% by weight, and the diol is propylene glycol in an amount of is 5% to 30% by weight.

10. An extract of *Gymnadenia conopsea*(L.)R.Br., wherein the extract is prepared by a method for extracting *Gymnadenia conopsea*(L.)R.Br., and the method comprises the following steps:

(1) the root tuber of *Gymnadenia conopsea*(L.)R.Br. is soaked in water so that it can be fully infiltrated until being taken as a sample, wherein no white core is observed in the root tuber of *Gymnadenia conopsea* (L.)R.Br.;

(2) the soaked root tuber of *Gymnadenia conopsea*(L.) R.Br. is ultrafinely comminuted by wet method to obtain a dispersion slurry;

(3) additional water is supplemented into the dispersion slurry to a obtain diluted dispersion followed by heating of the diluted dispersion and adding neutral protease to the diluted dispersion, and then extraction is carried out through circulation and homogenization with a homogenization pump in order to obtain extracted material fluid;

(4) the extracted material fluid is treated through heat preservation and enzyme inactivation;

(5) the extracted material fluid is subjected to coarse filtration to obtain a coarse filtrate; and (6) the coarse filtrate is subjected to fine filtration in order to obtain a fine filtrate.

11. The extract of *Gymnadenia conopsea*(L.)R.Br. as claimed in claim 10, wherein in the step (1), the volume (by liter) of water is 40-60 times of the weight (by kilogram) of the root tuber of *Gymnadenia conopsea*(L.)R.Br.; or, the temperature of the water is kept between 40° C. and 60° C.

12. The extract of *Gymnadenia conopsea*(L.)R.Br. as claimed in claim 10, wherein in the step (2), the ultrafine comminution by wet method is carried out by an ultra-fine crusher used for wet method of traditional Chinese medicine; or, the particle size of the dispersion slurry is 60 to 100 mesh.

13. The extract of *Gymnadenia conopsea*(L.)R.Br. as claimed in claim 10, wherein in the step (3), the volume (by liter) of water contained in the diluted dispersion is 40-100 times of the weight (by kilogram) of the root tuber of *Gymnadenia conopsea*(L.)R.Br.; or, the diluted dispersion is heated to 40° C. to 60° C..; or, the neutral protease is added in an amount of 0.01% to 1.0% (by weight) relative to the weight of the root tuber of *Gymnadenia conopsea*(L.)R.Br.; or, the extracted material fluid has the particle size of 100 to 500 mesh; or the duration of extraction is 1 to 6 hours.

14. The extract of *Gymnadenia conopsea*(L.)R.Br. as claimed in claim 10, wherein in the step (4), the temperature of heat preservation and enzyme inactivation is 75° C. to 90° C., and the duration of heat preservation and enzyme inactivation is 15 to 30 minutes; or, in step (5), the coarse filtration is a pressure filtration by using a filter cloth with 400 to 1000 mesh and a medium speed filter paper; or, in step (6), the fine filtration is carried out through a filter core with 0.2 to 0.45 μm.

15. The extract of *Gymnadenia conopsea*(L.)R.Br. as claimed in claim 10, which is characterized after the step (6), the extraction method further includes the following steps:
- (7-1) the fine filtrate is concentrated to obtain a concentrated fluid;
- (7-2) ethanol is added in the concentrated fluid to obtain a precipitate and a supernatant;
- (7-3) the precipitate is washed with ethanol to obtain an eluent, and then the precipitate is dried to obtain the *Gymnadenia conopsea*(L.)R.Br. polysaccharide; and
- (7-4) the supernatant is combined with the eluent followed by recovery under reduced pressure with dealcoholize, and butanediol is added thereto, whereby an extract fluid of *Gymnadenia conopsea*(L.)R.Br. is obtained.

16. The extract of *Gymnadenia conopsea*(L.)R.Br. as claimed in claim 15, wherein in the step (7-1), the volume (by liter) of the concentrated fluid is 10-40 times of the weight (by kilogram) of the root tuber of *Gymnadenia conopsea*(L.)R.Br.; or, in the step (7-2), the ethanol has a concentration of 70% (v/v) or more; or, in the step (7-3), the drying is freeze drying, vacuum drying or hot air circulation drying; or, in the step (7-4), the butanediol is added in an amount of 5% to 50% by weight.

17. The extract of *Gymnadenia conopsea*(L.)R.Br. as claimed in claim 10, wherein after the step (6), the method further includes the following steps:
- (8-1) the fine filtrate is concentrated to obtain a concentrated fluid;
- (8-2) the concentrated fluid is subjected to heat preservation and sterilization followed by a second fine filtration to obtain a second fine filtrate; and
- (8-3) organic acids and/or diols are added into the second fine filtrate in order to obtain an extract fluid of *Gymnadenia conopsea*(L.)R.Br. polysaccharide complex free of preservative.

18. The extract of *Gymnadenia conopsea*(L.)R.Br. as claimed in claim 17, wherein in the step (8-1), the volume (by liter) of the concentrated fluid is 10-40 times of the weight (by kilogram) of the root tuber of *Gymnadenia conopsea*(L.)R.Br.; or, in the step (8-2), the temperature of heat preservation and sterilization is 80° C. to 100° C., and the duration of heat preservation and sterilization is 15 to 30 minutes; or, the second fine filtration is carried out through a filter core with 0.2 to 0.45 μm; or, in the step (8-3), the organic acid is p-anisic acid in an amount of 0.05% to 0.4% by weight, and the diol is propylene glycol in an amount of is-5% to 30% by weight.

\* \* \* \* \*